United States Patent [19]

Karanewsky

[11] Patent Number: 5,504,080

[45] Date of Patent: Apr. 2, 1996

[54] BENZO-FUSED LACTAMS

[75] Inventor: Donald S. Karanewsky, Chapel Hill, N.C.

[73] Assignee: Bristol-Myers Squibb Co., Princeton, N.J.

[21] Appl. No.: 100,408

[22] Filed: Sep. 22, 1993

Related U.S. Application Data

[63] Continuation-in-part of Ser. No. 967,344, Oct. 28, 1992, abandoned.

[51] Int. Cl.$^6$ .................. C07D 487/06; A61K 31/55
[52] U.S. Cl. .................. 514/214; 514/80; 540/487; 540/520
[58] Field of Search .................. 540/487, 520; 514/80, 214

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,337,201 | 6/1982 | Petrillo | 548/413 |
| 4,339,600 | 7/1982 | Ondetti et al. | 562/426 |
| 4,374,829 | 2/1983 | Harris et al. | 424/177 |
| 4,410,520 | 10/1983 | Watthey | 424/244 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky | 424/200 |
| 4,461,896 | 7/1984 | Portlock | 546/165 |
| 4,487,716 | 12/1984 | Sarantakis | 260/112.5 |
| 4,567,177 | 1/1986 | Bigg et al. | 514/214 |
| 4,584,294 | 4/1985 | Ruyle | 514/214 |
| 4,680,392 | 7/1987 | Harris et al. | 540/527 |
| 4,684,660 | 8/1987 | Ondetti et al. | 514/423 |
| 4,749,688 | 6/1988 | Haslanger et al. | 514/19 |
| 4,801,609 | 1/1989 | Haslanger et al. | 514/506 |
| 4,816,466 | 3/1989 | Sugihara et al. | 546/195 |
| 4,871,842 | 10/1989 | Sugihara et al. | 540/523 |
| 4,873,235 | 10/1989 | Parsons et al. | 514/312 |
| 4,954,625 | 9/1990 | Sugihara et al. | 540/500 |
| 5,061,710 | 10/1991 | Haslanger et al. | 514/266 |
| 5,075,302 | 12/1991 | Neustadt | 514/211 |
| 5,238,924 | 8/1993 | Smith | 514/19 |
| 5,262,436 | 11/1993 | Haslanger et al. | 514/513 |
| 5,362,727 | 11/1994 | Robl | 514/214 |
| 5,366,973 | 11/1994 | Flynn et al. | 514/221 |

FOREIGN PATENT DOCUMENTS

| | | |
|---|---|---|
| 481522 | 4/1992 | European Pat. Off. . |
| 524553 | 1/1993 | European Pat. Off. . |
| 534363 | 3/1993 | European Pat. Off. . |
| 534396 | 3/1993 | European Pat. Off. . |
| 534492 | 3/1993 | European Pat. Off. . |
| 599444 | 6/1994 | European Pat. Off. . |
| 629627 | 12/1994 | European Pat. Off. . |
| 3708484 | 9/1987 | Germany . |
| 2086390 | 5/1982 | United Kingdom . |
| 2207351 | 2/1989 | United Kingdom . |
| WO04/10193 | 5/1994 | WIPO . |
| WO94/26719 | 11/1994 | WIPO . |

OTHER PUBLICATIONS

Blake et al., J. Am. Chem. Soc., 88, pp. 4061–4068 (1966).
Blake et al., J. Am. Chem. Soc., 87, pp. 1397–1398 (1965).
Watthey et al., J. Med. Chem., 27, pp. 816–818 (1984).
Delaney et al, Bioorganic & Medicinal Chem. Letters, 4, pp. 1783–1788 (1994).
Robl et al., Bioorganic & Medicinal Chem. Letters, 4, pp. 1789–1794, 1795–1800, 2055–2060 (1994).
Das et al., Bioorganic & Medicinal Chem. Letters, 4, pp. 2193–2198 (1994).
Robl, Tetrahedron Letters, 35, pp. 393–396, 1393–1396 (1994).
Robl et al, J. Am. Chem. Soc., 116, pp. 2348–2355 (1994).
Yoshitomi, Abstract of Japanese Application 2134378 (1990).

*Primary Examiner*—Philip I. Datlow
*Attorney, Agent, or Firm*—Stephen B. Davis

[57] ABSTRACT

Compounds of the formula

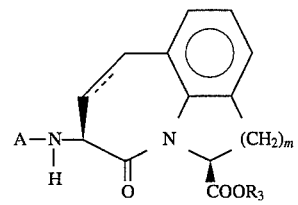

wherein A is

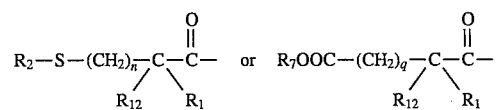

are useful as ACE and NEP inhibitors and those wherein A is

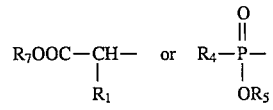

are useful as ACE inhibitors. Methods of preparation and intermediates are also disclosed.

31 Claims, No Drawings

BENZO-FUSED LACTAMS

RELATED APPLICATION

This application is a continuation-in-part of Ser. No. 967,344 filed Oct. 28, 1992, now abandoned.

BACKGROUND OF THE INVENTION

Captopril, (S)-1-(3-mercapto-2-methyl-1-oxopropyl)-L-proline, having the structural formula

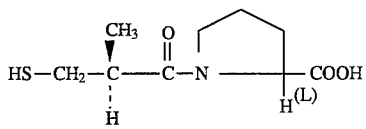

is an orally active angiotensin converting enzyme inhibitor useful for treating hypertension and congestive heart failue. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

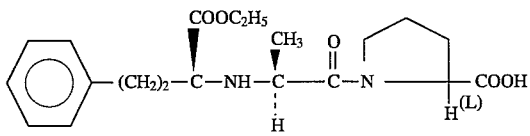

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S)-4-cyclohexyl-1-[[(R)-[(S)-1-hydroxy-2-methylpropoxy](4-phenylbutyl)-phosphinyl]acetyl]-L-proline propionate (ester), sodium salt having the structural formula

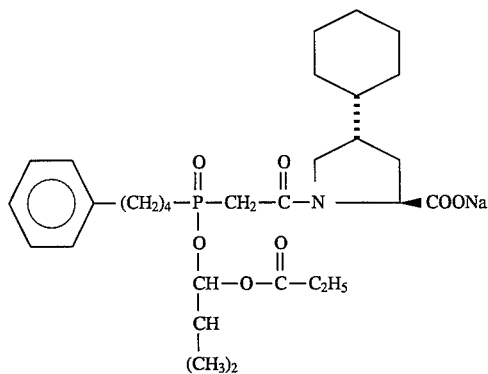

is also an orally active angiotensin converting enzyme inhibitor useful for treating hypertension. See Petrillo U.S. Pat. No. 4,337,201.

Haslanger et al. in U.S. Pat. No. 4,749,688 disclose treating hypertension by administering neutral metalloendopeptidase inhibitors alone or in combination with atrial peptides or angiotensin converting enzyme inhibitors.

Neustadt in U.S. Pat. No. 5,075,302 disclose that mercaptoacyl amino lactams of the formula

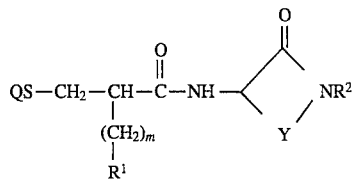

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt disclose employing such compounds alone or in combination with angiotensin converting enzyme inhibitors to treat cardiovascular diseases such as hypertension, congestive heart failure, edema, and renal insufficiency.

Delaney et al. U.K. Patent 2,207,351 disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al. in European Patent Application 481,522 disclose dual inhibitors of enkephalinase and angiotensin converting enzyme of the formulas

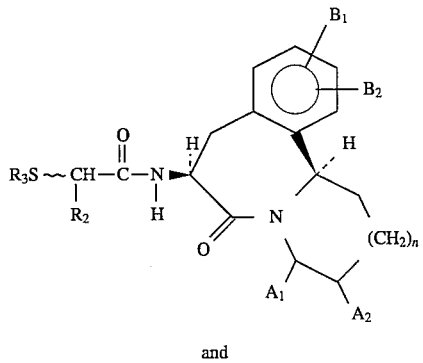

and

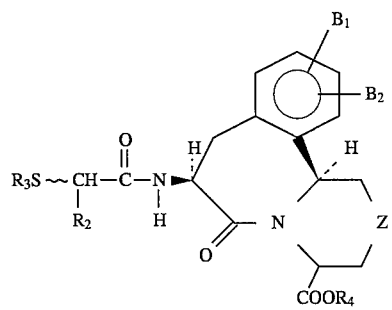

wherein n is zero or one and Z is O, S, —$NR_6$— or

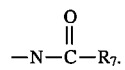

Additional tricyclic dual inhibitors are disclosed by Warshawsky et al. in European Patent Applications 534,363, 534,396 and 534,492.

Karanewsky et al. in U.S. Pat. Nos. 4,432,971 and 4,432,972 disclose phosphonamidate angiotensin converting enzyme inhibitors of the formula $$R_{21} - \overset{O}{\underset{|}{\overset{||}{P}}} - \overset{R_1}{\underset{|}{N}} - \overset{R_2}{\underset{|}{CH}} - \overset{O}{\overset{||}{C}} - X$$
$$OR_3$$

wherein X is a substituted imino or amino acid or ester.

Karanewsky in U.S. Pat. No. 4,460,579 discloses angiotensin converting enzyme inhibitors including those of the formula $$R_7 - \overset{O}{\overset{||}{P}} - NH - X - \overset{R_1}{\underset{|}{CH}} - \overset{O}{\overset{||}{C}} - OR_2$$
$$OR_8$$

wherein X is a thiazine or thiazepine.

Ruyle in U.S. Pat. No. 4,584,294 disclose angiotensin converting enzyme inhibitors of the formula Parsons et al. in U.S. Pat. No. 4,873,235 disclose angiotensin converting enzyme inhibitors of the formula

SUMMARY OF THE INVENTION

This invention is directed to novel benzo-fused lactam containing compounds possessing angiotensin converting enzyme inhibition activity. Some of these compounds also possess neutral endopeptidase inhibitory activity. This invention is also directed to pharmaceutical compositions containing such selective or dual action inhibitors and the method of using such compositions. This invention is also directed to the process for preparing such novel compounds and novel intermediates.

The novel benzo-fused lactam containing inhibitors of this invention include those of the formula (I)

and pharmaceutically acceptable salts thereof wherein:

A is $R_2-S-(CH_2)_n-\overset{R_{12}}{\underset{R_1}{C}}-\overset{O}{\overset{||}{C}}-$, $R_7OOC-(CH_2)_q-\overset{R_{12}}{\underset{R_1}{C}}-\overset{O}{\overset{||}{C}}-$, $R_7OOC-\underset{R_1}{CH}-$, or $R_4-\overset{O}{\underset{OR_5}{\overset{||}{P}}}-$;

$R_1$ and $R_{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen, $$R_6-\overset{O}{\overset{||}{C}}-,$$

or $R_{11}-S-$;

$R_3$, $R_5$ and $R_7$ are independently selected from hydrogen, alkyl, substituted alkyl, aryl-$(CH_2)_p-$, substituted aryl-$(CH_2)_p-$, heteroaryl-$(CH_2)_p-$, $-\underset{R_8}{CH}-O-\overset{O}{\overset{||}{C}}-R_9$, and $-CH_2\overset{O}{\underset{R_{10}}{\diagup}}$;

$R_4$ is alkyl, cycloalkyl-$(CH_2)_p-$, substituted alkyl, aryl-$(CH_2)_p-$, substituted aryl-$(CH_2)_p-$, or heteroaryl-$(CH_2)_p-$;

$R_6$ is alkyl, substituted alkyl, cycloalkyl-$(CH_2)_p-$, aryl-$(CH_2)_p-$, substituted aryl-$(CH_2)_p-$, or heteroaryl-$(CH_2)_p-$;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl-$(CH_2)_p-$;

$R_{11}$ is alkyl, substituted alkyl, cycloalkyl-$(CH_2)_p-$, aryl-$(CH_2)_p-$, substituted aryl-$(CH_2)_p-$, heteroaryl-$(CH_2)_p-$, or $-S-R_{11}$ completes a symmetrical disulfide wherein $R_{11}$ is m is one or two;
n is zero or one;
p is zero of an integer from 1 to 6;
q is zero or an integer from 1 to 3; and
the dashed line - - - represents an optioonal double bond between the two carbons.

DETAILED DESCRIPTION OF THE INVENTION

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio, or carboxy.

The terms "lower alkoxy" and "lower alkylthio" refer to such lower alkyl groups as defined above attached to an oxygen or sulfur.

The term "cycloalkyl" refers to saturated rings of 3 to 7 carbon atoms with cyclopentyl and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbons having one double bond.

The term "substituted alkenyl" refers to such straight or branched radicals of 3 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy.

The term "alkylene" refers to straight or branched chain radicals having up to seven carbon atoms, i.e. —CH$_2$—, —(CH$_2$)$_2$—, —(CH$_2$)$_3$—, —(CH$_2$)$_4$—,

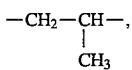

ect.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as

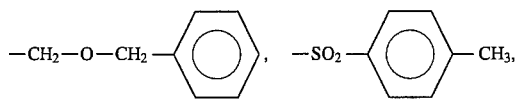

2,4-dinitrophenyl, lower alkyl, benzyl, or benzhydryl.

The compounds of formula I wherein A is

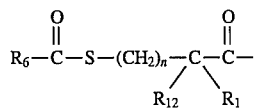

can be prepared by coupling the acylmercapto containing sidechain of the formula (II)

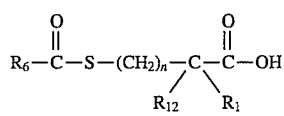

with a benzo-fused lactam of the formula (III)

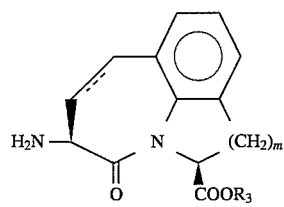

to give the product of the formula (IV)

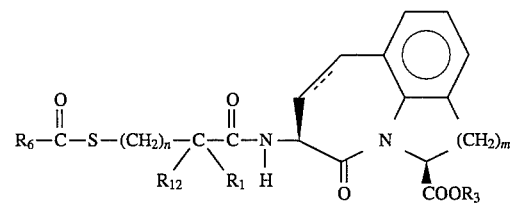

wherein R$_3$ is an easily removable ester protecting group such as methyl, ethyl, t-butyl, or benzyl. The above reaction can be performed in an organic solvent such as methylene chloride and in the presence of a coupling reagent such as 1-ethyl-3-(3-dimethylaminopropyl)carbodiimide, dicylcohexylcarbodiimide, benzotriazol-1-yloxytris(dimethylamino)phosphonium hexafluorophosphate, or carbonyldiimidazole. Alternatively, the acylmercapto carboxylic acid of formula II can be converted to an activated form prior to coupling such as an acid chloride, mixed anhydride, symmetrical anhydride, activated ester, etc.

The product of formula IV can be converted to the mercaptan product of formula I wherein R$_2$ is hydrogen and R$_3$ is hydrogen by methods known in the art. For example, when R$_6$ is methyl and R$_3$ is methyl or ethyl treatment with methanolic sodium hydroxide yields the products wherein R$_2$ and R$_3$ are hydrogen.

The products of formula I wherein $R_2$ is hydrogen can be acylated with an acyl halide of the formula (V)

$$R_6-\overset{O}{\underset{\|}{C}}-halo \quad\quad (V)$$

wherein halo is F, Cl or Br or acylated with an anhydride of the formula (VI)

$$R_6-\overset{O}{\underset{\|}{C}}-O-\overset{O}{\underset{\|}{C}}-R_6 \quad\quad (VI)$$

give other products of formula I wherein $R_2$ is $$R_6-\overset{O}{\underset{\|}{C}}-.$$

The products of formula I wherein $R_2$ is $-S-R_{11}$ and $R_{11}$ is alkyl, substituted alkyl, cycloalkyl-$(CH_2)_p-$, aryl-$(CH_2)_p-$, substituted aryl-$(CH_2)_p-$, or heteroaryl-$(CH_2)_p-$ can be prepared by reacting the products of formula I wherein $R_2$ is hydrogen with a sulfonyl compound of the formula (VII)

$$H_3C-SO_2-S-R_{11} \quad\quad (VII)$$

in an aqueous alcohol solvent to yield the desired products. The compounds of formula VII are known in the literature or can be prepared by known methods, see for example, Smith et al., Biochemistry, 14, p 766–771 (1975).

The symmetrical disulfide products of formula I can be prepared by direct oxidation of the product of formula I wherein $R_2$ is hydrogen with iodine as note, for example, Ondetti et al. U.S. Pat. No. 4,105,776.

The acylmercapto sidechain compounds of formula II wherein $R_{12}$ is hydrogen are described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, etc.

The acylmercapto sidechain compounds of formula II wherein $R_1$ and $R_{12}$ are both other than hydrogen and n is zero can be prepared by reacting the substituted carboxylic acid of the formula (VIII)

$$\underset{R_{12}}{\overset{}{\diagup}}\overset{}{\underset{R_1}{\diagdown}}HC-\overset{O}{\underset{\|}{C}}-OH \quad\quad (VIII)$$

with bis[(4-methoxy)phenyl]methyldisulfide in the presence of lithium diisopropylamide to give the compound of the formula (IX)

$$H_3CO-\underset{}{\bigcirc}-H_2C-S-\underset{R_{12}\;R_1}{\overset{}{C}}-\overset{O}{\underset{\|}{C}}-OH. \quad (IX)$$

Treatment of the compound of formula IX with strong acid such as trifluoromethanesulfonic acid removes the methoxybenzyl protecting group and is followed by acylation with the acyl halide of formula V or anhydride of formula VI to give the compound of formula II wherein $R_1$ and $R_{12}$ are both other than hydrogen and n is zero.

The acylmercapto sidechain compounds of formula II wherein $R_1$ and $R_{12}$ are both other than hydrogen and n is one can be prepared by reacting the substituted carboxylic acid of the formula (X)

$$HO-CH_2-\underset{R_{12}\;R_1}{\overset{}{C}}-\overset{O}{\underset{\|}{C}}-OH \quad\quad (X)$$

with para-toluenesulfonyl chloride in pyridine to give the lactone of the formula (XI)

$$\text{(XI lactone structure with } R_1, R_{12}\text{)}$$

Treatment of the lactone of formula XI with a cesium thioacid of the formula (XII)

$$Cs-S-\overset{O}{\underset{\|}{C}}-R_6 \quad\quad (XII)$$

in the presence of dimethylformamide yields the desired acylmercapto sidechain of formula II wherein $R_1$ and $R_{12}$ are both other than hydrogen and n is one.

The compounds of formula I wherein A is $$R_7OOC-(CH_2)_q-\underset{R_{12}\;R_1}{\overset{}{C}}-\overset{O}{\underset{\|}{C}}-,$$

can be prepared by coupling the acid of the formula (XIII)

$$R_7OOC-(CH_2)_q-\underset{R_{12}\;R_1}{\overset{}{C}}-\overset{O}{\underset{\|}{C}}-OH \quad (XIII)$$

wherein $R_7$ is an ester protecting group with the benzo-fused lactam of formula III in the presence of a coupling reagent as defined above to give the product of the formula (XIV)

$$R_7OOC-(CH_2)_q-\underset{R_{12}\;R_1}{\overset{}{C}}-\overset{O}{\underset{\|}{C}}-\underset{H}{\overset{}{N}}-\text{[benzo-fused lactam]} \quad (XIV)$$

Alternatively, the acid of formula XIII can be converted to an activated form such as an acid chloride prior to the coupling reaction.

The acids of formula XIII are described by Warshawsky et al. in European Patent Application 534,396 and 534,492.

The compounds of formula I wherein A is $$R_7OOC-\underset{R_1}{\overset{}{\underset{|}{CH}}}-$$

can be prepared by reacting a keto acid or ester of the formula (XV)

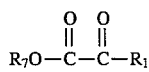

with a benzo-fused lactam of formula III under reducing conditions to give the product of the formula (XVI)

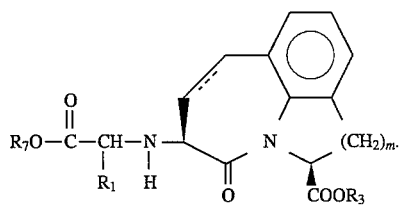

The keto acids and esters of formula XV are described in the literature. See, for example, Ruyle U.S. Pat. No. 4,584,294 and Parsons et al. U.S. Pat. No. 4,873,235.

Alternatively, the benzo-fused lactam compound formula III can be reacted with a triflate of the formula (XVII)

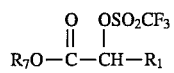

to give the product of formula XVI.

The compounds of formula I wherein A is

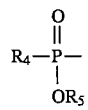

can be prepared by coupling a phosphonochloridate of the formula (XVIII)

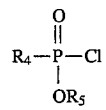

wherein $R_5$ is lower alkyl or benzyl with a benzo-fused lactam of formula III to give the product of the formula (XIX)

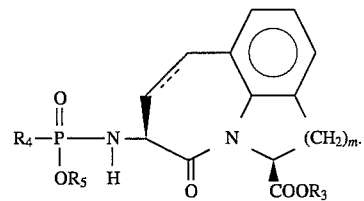

Preferably, the compound of formula III is in its hydrochloride salt form and $R_3$ is lower alkyl or benzyl. The $R_3$ and $R_5$ ester protecting groups can be removed, for example, by hydrogenation to give the corresponding products of formula I wherein $R_3$ and $R_5$ are hydrogen.

The phosphonochloridates of formula XVIII are known in the literature. See, for example, Karanewsky et al. U.S. Pat. Nos. 4,432,971 and 4,432,972 and Karanewsky U.S. Pat. No. 4,460,579.

The ester products of formula I wherein $R_5$ or $R_7$ is

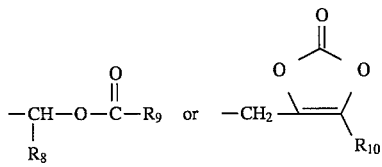

can be prepared by treating the corresponding compounds of formula I wherein $R_5$ or $R_7$ is hydrogen and $R_3$ is an ester protecting group with a compound 5 of the formula (XX)

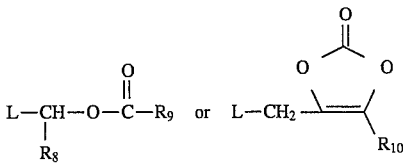

wherein L is a leaving group such as chloro, bromo, or tolylsulfonyloxy followed by removal of the $R_3$ ester protecting group.

The ester products of formula I wherein $R_3$ is

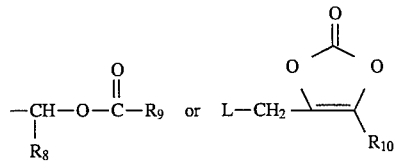

can be prepared by treating the corresponding compounds of formula I wherein $R_3$ is hydrogen and $R_2$ is

with a compound of formula XX.

The benzo-fused lactams of formula III can be prepared according to the following process which also forms part of this invention. An N-protected aspartic acid, γ-ester such as the N-phthalimido compound of the formula (XXI)

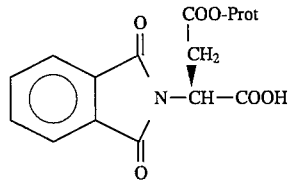

is converted to an activated form and reacted with the indole or quinoline ester of the formula (XXII)

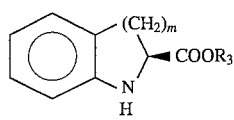

to give the compound of the formula (XXIII)

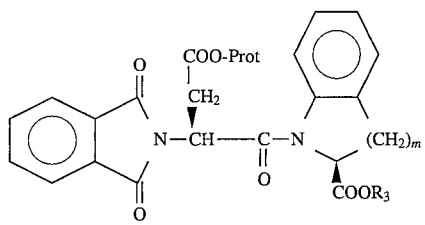

wherein Prot is a protecting group which can be selectively removed in the presence of the $R_3$ ester group. For example, when $R_3$ is methyl or ethyl and Prot is benzyl, the compound of formula XXIII can be hydrogenated to selectively remove the benzyl protecting group and yield the butanoic acid of the formula (XXIV)

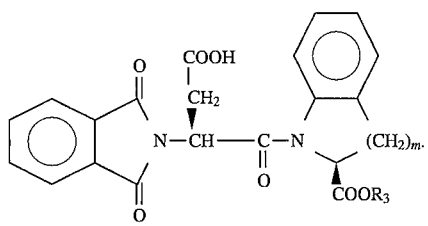

The butanoic acid of formula XXIV is converted to the corresponding butanethioic acid, ethyl ester and then to the corresponding butanal. Treatment with tri(lower alkyl)orthoformate gives the compound of the formula (XXV)

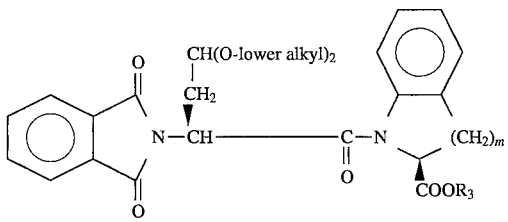

When m is one, the di(lower alkoxy) compound of formula XXV is cyclized by treatment with acids such as polyphosphoric acid and heat to give (XXVI)

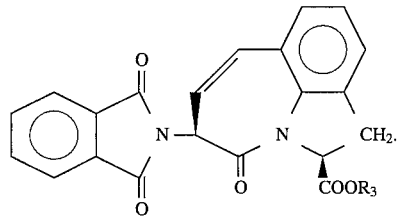

The N-phthalimido compound of formula XXVI can be hydrogenated and treated with hydrazine hydrate to give the benzo-fused lactam of formula III without the optional bond, i.e.

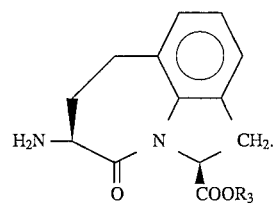

Alternatively, the N-phthalimido compound of formula XXVI can be treated with hydrazine hydrate to give the benzo-fused lactam of formula III containing the optional bond, i.e.,

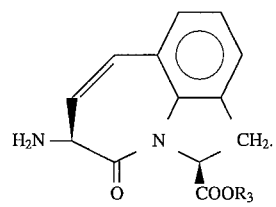

When m is two, the di(lower alkoxy) compound of formula XXV is cyclized by treatment with acids such as polyphosphoric acid and heat to give a mixture of (XXVII)

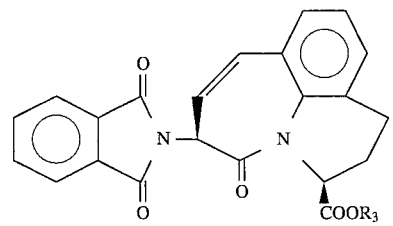

(XXVIII)

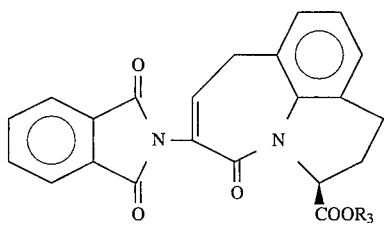

The N-phthalimido compound of formula XXVIII can be hydrogenated and treated with hydrazine hydrate to give the benzo-fused lactam of formula III wherein m is two without the optional double bond, i.e.,

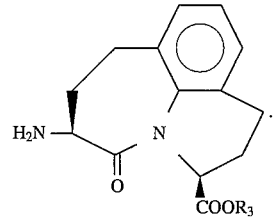

Alternatively, the N-phthalimido compound of formula XXVII can be treated with hydrazine hydrate to give the benzo-fused lactam of formula III wherein m is two containing the optional bond, i.e.,

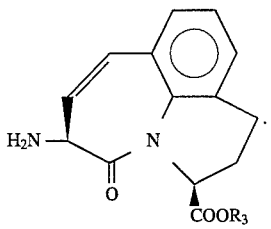

The compounds of formula I contain two asymmetric centers in the benzo-fused lactam portion of the structure with an additional center possible in the side chain. While the optically pure form of the benzo-fused lactam described above is preferred, all such forms are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I wherein $R_3$, $R_5$ and/or $R_7$ are hydrogen can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

Preferred compounds of this invention are those wherein:

A is

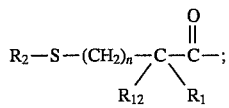

$R_2$ is hydrogen,

or $R_{11}$—S—;

$R_3$ is hydrogen or lower alkyl of 1 to 4 carbons;

n is zero or one;

$R_{12}$ is hydrogen;

$R_{11}$ is lower alkyl of 1 to 4 carbons;

$R_1$ is aryl-$CH_2$—, substituted aryl-$CH_2$—, heteroaryl-$CH_2$—, cycloalkyl-$CH_2$— wherein the cycloalkyl is of 5 to 7 carbons, or straight or branched chain alkyl of 1 to 7 carbons;

$R_6$ is lower alkyl of 1 to 4 carbons or phenyl; and m is one or two.

Most preferred are the above compounds wherein:

$R_2$ is hydrogen or

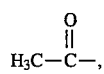

especially hydrogen;

$R_3$ is hydrogen;

n is zero;

$R_1$ is benzyl; and m is one or two.

The compounds of formula I wherein A is

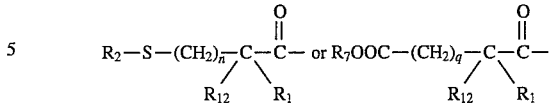

are dual inhibitors possessing the ability to inhibit angiotensin converting enzyme and neutral endopeptidase. The compounds of formula I wherein A is

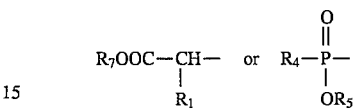

are selective inhibitors possessing the ability to inhibit the angiotensin converting enzyme. Thus, all of the compounds of formula I including their pharmaceutically acceptable salts are useful in the treatment of physiological conditions in which angiotensin converting enzyme inhibitors have been shown to be useful. Such conditions include disease states characterized by abnormalities in blood pressure, intraocular pressure, and renin including cardiovascular diseases particularly hypertension and congestive heart failure, glaucoma, and renal diseases such as renal failure. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases, glaucoma, as well as the relief of acute or chronic pain. Thus, the compounds of formula I are useful in reducing blood pressure and the dual inhibitors of formula I are additionally useful for this purpose due to their diuresis and natriuresis properties. The compounds of formula I including their pharmaceutically acceptable salts can be administered for these effects to a mammalian host such as man at from about 1 mg. to about 100 mg. per kg. of body weight per day, preferably from about 1 mg. to about 50 mg. per kg. of body weight per day. The compounds of formula I are preferably administered orally but parenteral routes such as subcutaneous, intramuscular, and intravenous can also be employed as can topical routes of administration. The daily dose can be administered singly or can be divided into two to four doses administered throughout the day.

The inhibitors of formula I can be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The inhibitors of formula I can be administered in combination with other classes of pharmaceutically active compounds. For example, a calcium channel blocker, a potassium channel activator, a cholesterol reducing agent, etc.

The inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

[2S-[2α,5α(R*)]]-1,2,4,5,6,7-Hexahydro-5-[(2 -mercapto-1-oxo-3-phenylpropyl)amino]-4-oxoazepino [3,2,1-hi]indole-2-carboxylic acid a) (S)-β-Carboxy-N-phthalimidepropanoic acid, phenylmethyl ester, dicyclohexylamine salt N-Carbethoxyphthalimide (23.0 g., 105 mmol.) was added in one portion to a solution of L-aspartic acid, γ-phenylmethyl ester (22.3 g., 100 mmol.) in aqueous sodium bicarbonate (10.6 g., 100 mmol. in 240 ml. of water)—dioxane (160 ml.) at room temperature. After stirring at room temperature for 2.5 hours, an additional 2.0 g. of N-carbethoxyphthalimide was added. After stirring at room temperature for an additional 1.5 hours, the resulting mixture was acidified with solid potassium bisulfate. The mixture was extracted with ethyl acetate, the organic phase washed with 5% potassium bisulfate and saturated sodium chloride solutions; dried (sodium sulfate) and evaporated to dryness. The crude acid was taken up in ethyl ether (400 ml.) and treated with dicyclohexylamine (20.0 ml, 101 mmol). After standing at room temperature for 16 hours, the crystalline dicyclohexylamine salt was collected, washed with ethyl ether and air-dried to give 46.35 g. of the title compound as a white, crystalline solid; m.p. 135°–137°; $[\alpha]_D$= −21.8° (c=1.1, chloroform). TLC (acetic acid:methanol:methylene chloride, 1:1:20) $R_f$=0.63.

b) (S)-β-(Fluorocarbonyl)-N-phthalimidepropionic acid, phenylmethyl ester

The dicyclohexylamine salt from part (a) (4.94 g., 9.25 mmol.) was partitioned between ethyl acetate-5% potassium bisulfate (60 ml. each). The organic phase was washed with 5% potassium bisulfate(3×30 ml.) and saturated sodium chloride solution, dried (sodium sulfate) and evaporated to dryness. The free acid (oil) was taken up in dry methylene chloride (25 ml.) and treated with pyridine (0.78 ml., 9.7 mmol) and cyanuric fluoride (0.92 ml., 10.9 mmol). After stirring at room temperature for 3.5 hours, the reaction was diluted with ethyl acetate and filtered, The filtrate was washed with cold, half-saturated sodium bicarbonate, 5% potassium bisulfate and saturated sodium chloride solutions; dried (sodium sulfate) and evaporated to dryness. The crude acid fluoride (oil) was used immediately without further purification.

c) (S)-2,3-Dihydro-1H-indole-2-carboxylic acid, ethyl ester, hydrochloride salt

A suspension of (S)-indoline-2-carboxylic acid (6.02 g., 36.9 mmol.) in ethanol (70 ml.) at 0° was saturated with hydrochloric acid and allowed to warm to room temperature. After 3 hours at room temperature, the resulting clear, red solution was purged with nitrogen and diluted with ethyl ether (200 ml.). The crystallized product was collected, washed with ethyl ether and dried in vacuo to give 6.43 g. of the title compound as white needles, m.p. 168°–169°; $[\alpha]_D$=−70.7° (c=0.68, chloroform). TLC (ethyl acetate-hexane, 1:1) $R_f$=0.63 (as free base).

d) [1(S),2S]-2-(Ethoxycarbonyl)-2,3-dihydro-γ-oxo-β-phthalimido-1H-indole-1-butanoic acid, phenylmethyl ester The hydrochloride salt product from part (c) (2.72 g., 12.0 mmole) was partitioned between ethyl acetate-saturated sodium bicarbonate (30 ml. each). The organic phase was washed with saturated sodium bicarbonate and saturated sodium chloride solutions, dried (sodium sulfate) and evaporated to dryness. The free base (oil) was taken up in dry methylene chloride (10 ml.), treated with 2,6-di(t-butyl)pyridine (2.1 ml., 9.35 mmol) and added to a solution of crude (S)-β-(fluorocarbonyl)-N-phthalimidepropionic acid, phenylmethyl ester from part (b) in dry methylene chloride (20 ml.) at −25° (dry ice-carbon tetrachloride) under argon. The resulting solution was kept at −25° (freezer) for 18 hours, then partitioned between ethyl acetate −5% potassium bisulfate. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-hexane (3:7) to give 4.44 g. of the title compound as a colorless foam. TLC (ethyl acetate-hexane, 3:2) $R_f$=0.52.

e) [1(S),2S]-2-Ethoxycarbonyl-2,3-dihydro-γ-oxo-β -phthalimido-1H-indole-1-butanoic acid A solution of the product from part (d) (9.6 g., 18.2 mmol.) in ethyl acetate (80 ml.) was treated with 20% palladium hydroxide on carbon catalyst and hydrogenated on a Parr apparatus at 35 psi for 6 hours. The mixture was filtered through Celite®, and the filtrate was evaporated to dryness to give 8.77 g. (110% of theory) of the title compound as a colorless foam. This crude product was used without further purification. TLC (methanol-methylene chloride; 1:9) $R_f$=0.37.

f) [1(S),2S]-2-Ethoxycarbonyl-2,3-dihydro-γ-oxo-γ -phthalimido-1H-indole-1-butanethioic acid, S-ethyl ester To a solution of the crude product from part (e) (about 18.2 mmol.) in dry methylene chloride (50 ml.) at 0° under argon was added ethanethiol (3.5 ml., 47.3 mmol.), 4-dimethylaminopyridine (0.450 g., 3.7 mmol. ) and 1-ethyl-3-(3-dimethylaminopropyl) carbodiimide hydrochloride (3.85 g., 20.1 mmol. ). After stirring at 0° for 1.5 hours, additional carbodiimide (0.40 g.) was added. After stirring at 0° for an additional 30 minutes and at room temperature for 1 hour, the mixture was evaporated to dryness. The residue was partitioned between ethyl acetate-5% potassium bisulfate. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-toluene (4:26) gave 7.05 g. of the title compound as a white crystalline solid, m.p. 174°–175°, after trituration with ethyl ether-hexane. TLC(ethyl acetate-hexane; 1:1) $R_f$=0.30. $[\alpha]_D$=−224.4° (c=0.66, chloroform).

g) [1(S),2S]-2-(Ethoxycarbonyl)-2,3-dihydroxy-γ-oxo-β-phthalimido-1H-indole-1-butanal Triethylsilane (4.16 ml., 26.0 mmol.) was added dropwise over 10 minutes to a suspension of 10% palladium on carbon (0.96 g.) in a solution of the product from part (f) (6.40 g., 12.9 mmol.) in dry acetonitrile (80 ml.). After stirring at room temperature for 45 minutes, the mixture was filtered through Celite® and evaporated to dryness. The residue was taken up in ethyl acetate and filtered through a pad of silica gel eluting with ethyl acetate. The filtrate was evaporated to dryness and the residue triturated with ethyl ether to give 3.95 g. of pure title compound as a white crystalline solid, m.p. 171°–172°. TLC (ethyl acetate-toluene, 25:75) $R_f$=0.30. $[\alpha]_D$=−245° (c=0.57, chloroform).

h) [1(S),2S]-1-(4,4-Diethoxy-1-oxo-2 -phthalimidobutyl)-2, 3-dihydro-1H-indole-2-carboxylic acid, ethyl ester To a solution of the product from part (g) (5.92 g., 14.3 mmol.) in ethanol (48 ml.)-methylene chloride (32 ml.) at room temperature under argon was added triethylorthoformate (4.8 ml.) followed by p-toluenesulfonic acid, monohydrate (0.060 g.). After stirring at room temperature for 2.5 hours, the reaction was quenched with saturated sodium bicarbonate (2.0 ml.) solution and concentrated to a small volume. The residue was partitioned between ethyl acetate-water, the organic phase was washed with saturated sodium bicarbonate and saturated sodium chloride solutions; dried (sodium sulfate) and evaporated to dryness. The crude product was combined with that of a small scale reaction [starting from 0.740 g. of the product from part (g)] and purified by flash chromatography on silica gel (Whatman LPS-1) eluting with ethyl acetate-hexane (25:75) to give 7.67 g. of the title compound as a colorless foam. TLC (ethyl acetate-hexane; 65:35) $R_f$=0.58.

i) (2S-cis)-5-Phthalimido-1,2,4,5-tetrahydro-4 -oxoazepino[3,2,1-hi]indole-2-carboxylic acid, ethyl ester A mixture of the product from part (h) (5.54 g., 11.2 mmol.) and polyphosphoric acid (55.8 g) was heated at 100° C. (bath temp) under argon for 30 minutes. The reaction was quenched with ice-water, the resulting tan precipitate collected, washed with water and air-dried. The solid was taken up in methylene chloride, washed with water, dried (sodium sulfate) and evaporated to dryness. The resulting yellow semi-solid was combined with the crude product of a smaller run starting with 2.0 g. of the product from part (h), taken up in methylene chloride, and filtered through a pad of silica gel eluting with ethyl acetate-toluene (1:9). The eluate was evaporated and the solid residue recrystallized from ethyl acetate-hexane to give 5.17 g., of title compound as a fluffy, white crystalline solid, m.p. 249°–250°. TLC(ethyl acetate-toluene; 1:4) $R_f$=0.40. $[\alpha]_D$=–211.6° (c=0.57, chloroform).

j) (2S-cis)-5-Phthalimido-1,2,4,5,6,7-hexahydro-4 -oxoazepino[3,2,1-hi]indole-2-carboxylic acid, ethyl ester To a solution of the product from part (i) (3.0 g., 7.46 mmol.) in tetrahydrofuran (200 ml.)ethanol (50 ml.) was added 10% palladium on carbon (1.0 g.) and the resulting mixture stirred under a hydrogen atmosphere (balloon) for 6 hours. The mixture was filtered through Celite® and evaporated to dryness. The crude product was triturated with ethyl ether-hexane to give 2.92 g. of titled product as a white, crystalline solid, m.p. 174°–176°. TLC(ethyl acetate-methylene chloride; 5:95) $R_f$=0.29. $[\alpha]_D$=–151.5° (c=0.71, chloroform).

k) (2S-cis)-5-Amino-1,2,4,5,6,7-hexahydro-4-oxoazepino[3,2,1-hi]indole-2-carboxylic acid, ethyl ester A solution of the product from part (j) (2.64 g., 6.53 mmol.) in 1.0M hydrazine hydrate in ethanol (14.4 ml., 14.4 mmol.) was stirred at room temperature under argon. After stirring at room temperature for 8 hours, ethanol (10 ml.) was added to allow for greater ease of stirring. After a total of 32 hours, the mixture was diluted with an equal volume of ethyl acetate, filtered and the filtrate was evaporated to dryness. The residue was taken up in toluene, filtered and again evaporated to dryness. Purification of the crude product by flash chromatography on silica gel (Whatmann LPS-1) eluting with methanol-methylene chloride (5:100) gave 1.64 g. of crude product. Crystallization from ethyl ether-hexane gave 1.51 g. of pure title compound as a white, crystalline solid; m.p. 110°–111.5°. TLC (methanol-methylene chloride, 1:9) $R_f$=0.31. $[\alpha]_D$=–257.7° (c=0.51, chloroform).

l) (S)-2-(Acetylthio)benzenepropanoic acid, dicyclohexylamine salt

Sodium nitrite (10.3 g., 280 mmol.) was added to a solution of D-phenylalanine (30.0 g., 181 mmol.) and potassium bromide (73.5 g.) in sulfuric acid (2.5N, 365 ml.) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g. of (R)-2-bromo-3-benzenepropanoic acid; b.p. 141° (0.55 mm of Hg.); $[\alpha]_D$=+14.5° (c=2.4, chloroform).

A mixture of thioacetic acid (7 ml., 97.9 mmol.) and potassium hydroxide (5.48 g., 97.9 mmol.) in acetonitrile (180.5 ml.) was stirred under argon at room temperature for 1¾ hours. The mixture was cooled in an ice-bath, and a solution of (R)-2-bromo-3-benzenepropanoic acid (20.4 g., 89 mmol.) in acetonitrile (20 ml.) was added over a ten minute period. The reaction was stirred under argon at room temperature for 5 hours, filtered, and the acetonitrile was removed in vacuo. The oily residue was redissolved in ethyl acetate and washed with 10% potassium bisulfate and water. Removal of the ethyl acetate in vacuo afforded 19.6 g. of crude product. The crude product was purified via its dicyclohexylamine salt using isopropyl ether as solvent for crystallization. An analytical sample of (S)-2-(acetylthio)benzenepropanoic acid, dicyclohexylamine salt was prepared by recrystallization from ethyl acetate; m.p. 146°–147°; $[\alpha]_D$=–39.6° (c=1.39, chloroform).

Anal. calc'd. for $C_{11}H_{12}O_3S \cdot C_{12}H_{23}N$: C,68.11; H,8.70; N,3.45; S,7.91 Found: C,67.93; H,8.71; N,3.37; S,7.94.

m) [2S-[2α,5α(R*)]]-1,2,4,5,6,7-Hexahyro-5-[[2 -(acetylthio)-1-oxo-3-phenylpropyl]amino]-4 -oxoazepino[3,2,1-hi]indole-2-carboxylic acid, ethyl ester (S)-2-(Acetylthio)benzenepropanoic acid, dicyclohexylamine salt (1.04 g., 2.57 mmol.) was partitioned between ethyl acetate (30 ml.)-5% potassium bisulfate (30 ml.). The organic phase was washed with 5% potassium bisulfate (2×20 ml.) and saturated sodium chloride solutions, dried (sodiun sulfate) and evaporated to dryness. The resulting free acid (about 2.57 mmol.) was taken up in dry methylene chloride (15 ml.), placed in an ice bath and treated with hydroxybenzotriazole hydrate (0.37 g., 2.74 mmol.), the 5-amino product from part (k) (0.67 g., 2.45 mmol.) and 1-ethyl-3-(3-dimethylaminopropyl)carbodiimide hydrochloride (0.540 g., 2.82 mmol.). After stirring at 0° for 2.5 hours and at room temperature for 1 hour, the mixture was partitioned between ethyl acetate-water. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-toluene (1:9) gave 1.07 g. of crude product as a white solid. Recrystallization from ethyl acetate-hexane gave 0.99 g., of pure title compound as a white, crystalline solid, m.p. 138°–139.5°. TLC (ethyl acetate-toluene, 1:4) $R_f$=0.42. $[\alpha]_D$=–179.5° (c=0.56, chloroform).

n) [2S-[2α,5α(R*)]]-1,2,4,5,6,7-Hexahydro-5-[(2 -mercapto-1-oxo-3-phenylpropyl)amino]-4-oxoazepino-[3,2,1-hi]indole-2-carboxylic acid To a degassed solution of the product of part (m) (0.79 g., 1.65 mmol.) in methanol (15 ml.)-tetrahydrofuran (15 ml.) at 0° was added a degassed solution of 1.0N aqueous sodium hydroxide (10.0 ml., 10.0 mmol.). Throughout the course of the reaction, argon was continously passed into the reaction mixture. After stirring at 0° for 70 minutes, the reaction was quenched with concentrated hydrochloric acid (1.3 ml.) and extracted with ethyl acetate. The ethyl acetate extract was washed with saturated sodium chloride solution, dried (sodium sulfate) and evaporated to dryness. The crude product was triturated with ethyl ether, collected by suction and dried in vacuo at 50° to give 0.65 g., of title product as a white solid, m.p. 136°–138°. TLC (methylene chloride-acetic acid-methanol; 20:1:1) $R_f$=0.58. $[\alpha]_D$=−163.4° (c=0.50, methanol).

Calc'd. for $C_{22}H_{22}N_2O_4S\cdot0.26\ C_4H_{10}O$: C 64.39; H 5.77; N 6.52; S 7.46; SH 7.69; Found C 64.25; H 5.58; N 6.40; S 7.61; SH 8.11.

EXAMPLE 2

[2S-[2α,5α(R*)]]-1,2,4,5,6,7-Hexahydro-5-[[2 -(mercaptomethyl)-1-oxo-3-phenylpropyl]amino]-4-oxoazepino[3,2,1-hi]indole-2-carboxylic acid a) (S)-2-[(Acetylthio)methyl]benzenepropanoic acid, ephedrine salt A solution of (1R,2S)-(−)-ephedrine (17.3 g., 105 mmol.) in diethyl ether (175 ml.) was added in one portion to a solution of 2-[(acetylthio)methyl]benzenepropanoic acid (50.0 g., 210 mmol.) in diethyl ether (175 ml.). After standing at room temperature for 16 hours, the crystallized ephedrine salt was collected by filtration (19.7 g.); m.p. 114°– 125°; $[\alpha]_D$=−40.6° (c=1, methanol). An additional amount of solid [8.9 g., m.p. 121°–126°; $[\alpha]_D$=−47.2°, (c=1, methanol)] separated from the filtrate after remaining at room temperature for 20 hours. The solids were combined and recrystallized from acetonitrile (1500 ml.). After 16 hours at room temperature, 20.8 g. of solid was collected; m.p. 125°–130° C.; $[\alpha]_D$=−47.5° (c=1, methanol). This material was recrystallized in the same manner from acetonitrile (300 ml.) to give 18.74 g., m.p. 128°–130° C.; $[\alpha]_D$=−48.9° (c=1, methanol). A third recrystallization from acetonitrile (225 ml.) afforded 17.4 g. of solid (S)-2-[(acetylthio)methyl]benzenepropionic acid, ephedrine salt; m.p. 128°–129°; $[\alpha]_D$=−50.1° (c=1, methanol).

Anal. calc'd. for $C_{12}H_{14}O_3S\cdot C_{10}H_{15}NO$: C,65.48; H,7.24; N,3.47; S,7.95 Found: C,65.46; H,7.34; N,3.21; S,8.00.

b) [2S-[2α,5α(R*)]]-1,2,4,5,6,7-Hexahydro-5-[[2-[(acetylthio)methyl]-1-oxo-3-phenylpropyl]amino]-4-oxoazepino[3,2,1-hi]indole-2-carboxylic acid, ethyl ester The ephedrine salt product from part (a) (0.64 g., 1.58 mmol.) was partitioned between ethyl acetate (25 ml.)-aqueous hydrochloric acid (2.5 ml. 1.0N hydrochloric acid+ 15 ml. water). The organic phase was washed with aqueous hydrochloric acid (1.0 ml. 1.0N hydrochloric acid+10 ml. water) and saturated sodium chloride solutions, dried (sodium sulfate) and evaporated to dryness. The resulting free acid (about 1.58 mmol.) was taken up in dry methylene chloride (10.0 ml.), placed in an ice bath and treated with hydroxybenzotriazole hydrate (0.22 g., 1.59 mmol.), (2S-cis)-5-amino-1,2,4,5,6,7-hexahydro-4-oxoazepino[3,2,1-hi]indole-2-carboxylic acid, ethyl ester [0.41 g., 1.50 mmol., from Example 1(k)], and 1-ethyl-3-(3-dimethylaminopropyl)carbodiimide hydrochloride (0.320 g., 1.67 mmol.). After stirring at 0° for 3 hours and at room temperature for 3 hours, the mixture was partitioned between ethyl acetate-5% potassium bisulfate. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-hexane (40:110) gave 0.67 g., of the title product as a colorless foam. TLC (ethyl acetate-hexane; 1:1) $R_f$=0.48.

c) [2S-[2α,5α(R*)]]-1,2,4,5,6,7-Hexahydro-5-[[2 -(mercaptomethyl)-1-oxo-3-phenylpropyl]amino]-4-oxoazepino[3,2,1-hi]indole-2-carboxylic acid To a degassed solution of the product from part (b) (0.66 g., 1.34 mmol.) in methanol (10 ml.) at 0° was added a degassed solution of 1.0N aqueous sodium hydroxide (8.0 ml., 8.0 mmol.). Thoughout the course of the reaction, argon was continously passed into the reaction mixture. After stirring at 0° for 1.5 hours, the reaction was quenched with concentrated hydrochloric acid (1.0 ml.) and extracted with ethyl acetate. The ethyl acetate extract was washed with a saturated sodium chloride solution, dried (sodium sulfate) and evaporated to dryness. The crude product was triturated with ethyl ether-hexane, collected by suction and dried in vacuo to give 0.56 g. of title product as a white solid; m.p. 78°– 80° (became glass). TLC (methylene chloride-acetic acid-methanol; 40:1:1) $R_f$=0.37. $[\alpha]_D$=−146.2° (c=0.62, methanol).

Anal. calc'd. for $C_{23}H_{24}N_2O_4S\cdot0.3\ C_4H_{10}O\cdot0.17\ H_2O$: C 64.39; H 5.77; N 6.52; S 7.46; SH 7.69 Found: C 64.25; H 5.58; N 6.40; S 7.61; SH 8.11.

EXAMPLE 3

[2S-[[2α,5α(R*)]]-1,2,4,5-Tetrahydro-5-[(2-mercapto-1-oxo-3-phenylpropyl)amino]-4-oxoazepino [3,2,1-hi]indole-2-carboxylic acid a) (2S-cis)-5-Amino-1,2,4,5-tetrahydro-4-oxoazepino[3, 2,1-hi]indole-2-carboxylic acid, ethyl ester To a solution of (2S-cis)-5-phthalimido-1,2,4,5-tetrahydro-4-oxoazepino[3,2,1-hi]indole-2-carboxylic acid, ethyl ester [1.810 g., 4.50 mmol., from Example 1(i)] in ethanol (15 ml.) at room temperature under argon was added hydrazine hydrate (0.48 ml., 9.9 mmol.). After stirring at room temperature for 26 hours, the mixture was diluted with an equal volume of ethyl acetate, filtered and the filtrate was evaporated to dryness. The residue was taken up in toluene, filtered and again evaporated to dryness. Purification of the crude product by flash chromatography on silica gel (Whatmann LPS-1) eluting with methanol-methylene chloride (5:100) gave 0.85 g., of the title product as a white solid. Crystallization of the product from ethyl ether-hexane gave 0.82 g. of pure title product as a white, crystalline solid; m.p. 80°–82°. TLC (methanol:chloroform; 5:95; 2 developments) $R_f$=0.45. $[\alpha]_D$=−119.1° (c=0.52, chloroform).

b) [2S-[2α,5α(R*)]]-1,2,4,5-Tetrahydro-5-[[2 -(Acetylthio)-1-oxo-3-phenylpropyl]amino]-4-oxoazepino[3,2,1-hi]indole-2-carboxylic acid, ethyl ester (S)-2-(Acetylthio)benzenepropanoic acid, dicyclohexylamine salt (0.64 g., 1.58 mmol.) was partitioned between ethyl acetate (30 ml.)-5% potassium bisulfate (30 ml.). The organic phase was washed with 5% potassium bisulfate (2×20 ml.) and saturated sodium chloride solutions, dried (sodium sulfate) and evaporated to dryness. The resulting free acid (about 1.58 mmol.) was taken up in dry methylene chloride (10 ml.), placed in an ice bath and treated with hydroxybenzotriazole hydrate (0.224 g., 1.66 mmol.), the 5-amino product from part (a) 0.410 g, 1.51 mmol.) and 1-ethyl-3-(3-dimethylaminopropyl)carbodiimide hydrochloride (0.380 g., 1.98 mmol.). After stirring at 0° for 1.5 hours and at room temperature for 2 hours, the mixture was partitioned between ethyl acetate-5% potassium bisulfate. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-toluene (1:9) gave 0.553 g., of crude product as a foam. Mixed fractions (0.101 g). containing the desired product and its side chain epimer were also obtained from the chromatography. Crystallization of the product from ethyl etherhexane gave 0.530 g. of pure title product as a white, crystalline solid, m.p. 161.5°–162.5°. TLC (ethyl acetate-toluene; 1:4) $R_f$=0.47. $[\alpha]_D$=− 132.3° (c=0.56, chloroform).

c) [2S-[2α,5α(R*)]]-1,2,4,5-Tetrahydro-5-[2 -mercapto-1-oxo-3-phenylpropyl)amino]-4-oxoazepino[3,2,1-hi]indole-2-carboxylic acid To a degassed solution of the product from part (b) (0.48 g., 1.0 mmol.) in methanol (6 ml.)-tetrahydrofuran (4 ml.) at 0° was added a degassed solution of 1.0N aqueous sodium hydroxide (6.0 ml., 6.0 mmol.). Throughout the course of the reaction, argon was continously passed into the reaction mixture. After stirring at 0° for 45 minutes, the reaction was quenched with concentrated hydrochloric. The acid (0.7 ml.) and extracted with ethyl acetate. ethyl acetate extract was washed with saturated sodium chloride solution, dried (sodium sulfate) and evaporated to dryness. Purification of the crude product by flash chromatography on silica gel (Whatmann LPS-1) eluting with methylene chloride-acetic acid-methanol (100:0.2:4) to give 0.336 g., of the title product as a foam. Crystallization from methanol-ethyl ether gave 0.319 g., of pure title product as a white, crystalline solid, m.p. 210°–212°. TLC (methylene chloride-acetic acid-methanol; 40:1:1) $R_f$=0.24. $[\alpha]_D$=−148.0° (c=0.45, methanol).

Anal. calc'd. for $C_{22}H_{20}N_2O_4S$: C 64.69; H 4.93; N 6.86; S 7.85 Found: C 64.44; H 4.65; N 6.62; S 7.89.

EXAMPLE 4

[2S-[2α,5α(R*)]]-1,2,4,5-Tetrahydro-5-[[2-(mercaptomethyl)-1-oxo-3-phenylpropyl]amino]-4-oxoazepino[3,2,1-hi]indole-2-carboxylic acid a) [2S-{2α,5α(R*)]]-1,2,4,5-Tetrahydro-5-[[2-[(acetylthio)methyl]-1-oxo-3-phenylpropyl]amino]-4-oxoazepino[3,2,1-hi]indole-2-carboxylic acid, ethyl ester (S)-2-[(Acetylthio)methyl]benzenepropanoic acid, ephedrine salt [0.585 g., 1.45 mmol., from Example 2(a)] was partitioned between ethyl acetate (25 ml.)-aqueous hydrochloric acid (2.5 ml. 1.0N hydrochloric acid+25 ml. water). The organic phase was washed with aqueous hydrochloric acid (1.0 ml. 1.0N hydrochloric acid+10 ml. water) and saturated sodium chloride solutions, dried (sodium sulfate) and evaporated to dryness. The resulting free acid (about 1.45 mmol.) was taken up in dry methylene chloride (10.0 ml.), placed in an ice bath and treated with hydroxybenzotriazole hydrate (0.205 g., 1.52 mmol.), (2S-cis)-5-amino-1,2,4,5-tetrahydro-4-oxoazepino[3,2,1-hi]indole-2-carboxylic acid, ethyl ester [0.37 5 g., 1.38 mmol., from Example 3(a)] and 1-ethyl-3-(3-dimethylaminopropyl)carbodiimide hydrochloride (0.295 g., 1.54 mmol.). After stirring at 0° for 2 hours and at room temperature for 4 hours, the mixture was partitioned between ethyl acetate-5% potassium bisulfate. The organic phase was washed successively with 5% potassium bisulfate, saturated sodium bicarbonate and saturated sodium chloride solutions; dried (sodium sulfate) and evaporated to dryness. Purification of the crude product by flash chromatography on silica gel (Whatmann LPS-1) eluting with ethyl acetate-hexane (40:110) gave 0.596 g., of title product as a colorless foam. Crystallization from ethyl etherhexane gave 0.566 g., of pure title product as a white crystalline solid, m.p. 139°–141°. $[\alpha]_D$=−124.2° (c=0.54, chloroform). TLC (ethyl acetate:hexane; 1:1) $R_f$=0.42.

b) [2S-[2α,5α(R*)]]-1,2,4,5-Tetrahydro-5-[[2 -(mercaptomethyl)-1-oxo-3-phenylpropyl]amino]-4-oxoazepino[3,2,1-hi]indole-2-carboxylic acid To a degassed solution of the product from part (a) (0.505 g., 1.03 mmol.) in methanol (8.0 ml.) at 0° was added a degassed solution of 1.0N aqueous sodium hydroxide (6.0 ml., 6.0 mmol.). Throughout the course of the reaction, argon was continously passed into the reaction mixture. After stirring at 0° for 50 minutes, the reaction was quenched with concentrated hydrochloric acid (0.6 ml.). The resulting white solid was filtered off, washed with water and air-dried. The crude product was recrystallized from methanol-ethyl ether and dried in vacuo at 45° to give 0.334 g. of product as fine white needles; m.p. shrinks at about 98°, foams at about 108°–112°. The residue from the mother liquor (0.09 g.) was purified by flash chromatography on silica gel (Whatmann LPS-1) eluting with methylene chloride-acetic acid-methanol (100:0.2:4) to give 0.051 g. of additional product as a white solid. Crystallization of this material from methanol-ethyl ether gave 0.048 g. of crystalline product (total: 0.382 g.). TLC (methylene chloride-acetic acid-methanol; 40:1:1) $R_f$=0.33. $[\alpha]_D$=−129.0° (c=0.54, methanol).

Anal. calc'd. for $C_{23}H_{22}N_2O_4S \cdot 0.14 \ C_4H_{10}O \cdot 0.25 \ CH_4O \cdot 0.3 \ H_2O$: C 64.07; H 5.65; N 6.28; S 7.18 Found C 64.07; H 5.63; N 6.29; S 7.56.

EXAMPLE 5

[2S-(2α,5α)]-1,2,4,5,6,7-Hexahydro-5-[[2-mercapto-1-oxo-3-(naphthalenyl)propyl]amino]-4-oxoazepino[3,2,1-hi]indole-2-carboxylic acid a) (Acetylamino)(1-naphthalenylmethyl)propanedioic, diethyl ester To a solution of sodium ethoxide (21% by weight in ethanol, 4.613 g., 67.8 mmol.) in ethanol (100 ml) was added diethyl acetamidomalonate (14.74 g., 67.8 mmol.), then 1-(bromomethyl)napthalene (10.0 g., 45.2 mmol.). The solution was stirred at room temperature for one hour. The reaction mixture was then concentrated to an orange oil. The oil was dissolved in ethyl acetate and washed with 50% saturated ammonium chloride, water, and brine, then dried over sodium sulfate, filtered and concentrated to afford an orange solid. The solid was recrystallized from ethyl acetate and hexane to afford beige crystals contaminated with diethyl acetamido-malonate. The solid was dissolved in 50% ethyl acetate in hexane and purified by flash chromatography on Merck silica gel in 50% ethyl acetate in hexane. Those fractions containing pure product were combined and concentrated to afford 10.225 g. of product as a white solid; m.p. 105°–108°; $R_f$=0.57 (50% ethyl acetate in hexane).

b) α-Amino-1-naphthalenepropanoic acid

A solution of the product from part (a) (16.182 g., 47.5 mmol.) was suspended in 48% hydrogen bromide (100 ml.) and refluxed under argon for 14 hours. The hydrogen bromide salt of the product was filtered out of solution as a white solid, then taken up in hot (50°) water (500 ml.) and the solution neutralized with concentrated ammonium hydroxide. The product precipitated out of solution as a fine white solid. Upon filtration and drying under high vacuum overnight (18 hours), 8.335 g. of product was obtained as a fluffy white solid; m.p. 264°.

c) α-Bromo-1-naphthalenepropanoic acid

To a solution of the product from part (b) (4.00 g., 18.6 mmol) and potassium bromide (7.63 g., 63.2 mmol.) in 2.5N sulfuric acid (35 ml.) kept at 0° was added sodium nitrite (1.92 g., 27.8 mmol) over one hour. The mixture was stirred for an additional hour at 0°, then was warmed to room temperature and stirred for 2.5 hours. The reaction mixture was then extracted with ether (3×). The ether layers were combined and washed with water and brine, then dried over sodium sulfate, filtered and concentrated to give an orange oil. The oil was purified by flash chromatography on Merck silica gel in 70% ethyl acetate in hexane with 1% acetic acid. Those fractions containing the bromide were combined and concentrated to afford 2.13 g. of slightly contaminated product as an orange oil which solidified upon standing overnight. $R_f$=0.40 (40% ethyl acetate in hexane with 1% acetic acid).

d) α-(Acetylthio)-1-naphthalenepropanoic acid

To a slurry of potassium thioacetate (0.912 g., 8.00 mmol) in acetonitrile (300 ml.) at 0° was added the product from part (c) (2.030 g., 7.27 mmol) as a solution in-aceonitrile (3 ml.). The solution was stirred for one hour at 0°, then was warmed to room temperature and stirred for 15 hours. Potassium bromide was then filtered out of the reaction mixture and the filtrate concentrated to afford an orange oil. The oil was dissolved in ethyl acetate and washed with 10% potassium bisulfate and brine, then dried over sodium sulfate, filtered and concentrated to afford an orange oil. The oil was purified by flash chromatography on Merck silica gel in 50% ethyl acetate in hexane with 1% acetic acid. The desired fractions were pooled and concentrated to give an orange oil. The crude product was purified via the dicyclohexylamine salt by dissolving the orange oil in ether and adding an equivalent of dicyclohexylamine (18.13 g., 100 mmol.) to the solution. The dicyclohexylamine salt was obtained in 2 crops of brown crystals (1.450 g.) still slightly contaminated with an impurity. The crystals were suspended in ethyl acetate and shaken with 10% potassium bisulfate (3×). The organic layer was then washed with water and brine, then dried over sodium sulfate filtered and concentrated to afford 875 mg. of product as a yellow oil; $R_f$=0.40 (40% ethyl acetate in hexane with 1% acetic acid).

e) [2S-(2α,5α)]-1,2,4,5,6,7-Hexahydro-5-[[2-(acetylthio)-1-oxo-3-(1-naphthalenyl)propyl]amino]-4-oxoazepino[3,2,1-hi]indole-2-carboxylic acid, ethyl ester The racemic acid product from part (d) (338 mg., 1.23 mmol.) and (2S-cis)-5-amino-1,2,4,5,6,7-hexahydro-4-oxoazepino[3,2,1-hi]indole-2-carboxylic acid, ethyl ester [338 mg., 1.23 mmol., from Example 1(k)] were dissolved in methylene chloride (11 ml.) at room temperature under argon. The mixture was cooled to 0° and treated with hydroxybenzotriazole hydrate (166 mg., 1.23 mmol.) and 1-ethyl-3-(3 -dimethylaminopropyl)carbodiimide (259 mg., 1.35 mmol.). After stirring for one hour, the mixture was warmed to room temperature and stirred an additional 5 hours. The volatiles were evaporated and the residue was dissolved in ethyl acetate and washed successively with 1N hydrochloric acid, water, saturated sodium bicarbonate, and brine. The organic layer was dried (sodium sulfate), filtered and concentrated and the residue was flash chromatographed (Merck silica gel) eluting with 50% ethyl acetate in hexanes to give 660 mg. of the title compound as a clear oil (1:1 mixture of diastereomers). TLC (ethyl acetate:hexanes, 1:1) $R_f$=0.51 and 0.55.

f) [2S-(2α,5α)]-1,2,4,5,6,7-Hexahydro-5-[[2 -mercapto-1-oxo-3-(1-naphthalenyl)propyl]amino]-4-oxoazepino[3,2,1-hi]indole-2-carboxylic acid A solution of the product from part (e) (658 mg., 1.23 mmol.) in methanol (8 ml., deoxygenated via argon bubbling) was cooled to 0° and treated with 1N sodium hydroxide (8 ml., deoxygenated via argon bubbling). The resulting mixture was stirred under argon for 45 minutes. The solution was acidified with 10% potassium bisulfate and extracted with ethyl acetate. The organic layer was washed with brine, dried (sodium sulfate), filtered and concentrated to give a clear oil. This residue was flash chromatographed (Merck silica gel) eluting first with 1% acetic acid in 2:3 ethyl acetate:hexanes and then 1% acetic acid in 1:1 ethyl acetate:hexanes. The product containing fractions were combined, concentrated, azeotroped with ethyl acetate, and washed with water to remove acetic acid. The organic layer was dried (sodium sulfate), filtered, and concentrated. The residue was taken up in ethyl acetate and triturated with ethyl ether and hexane. The solvent was removed and the residue was slurried in hexane, stripped, and dried in vacuo to give 320 mg. of the title product as a white powdery foam. TLC (5% acetic acid in ethyl acetate) $R_f$=0.63. $[α]_D$=−170.6° (c=0.46, chloroform).

Anal. calc'd. for $C_{26}H_{24}N_2O_4S•0.45\ C_4H_8O_2$: C, 66.75; H, 5.56; N, 5.60; S, 6.41 Found: C, 66.61; H, 5.85; N, 5.22; S, 5.98.

EXAMPLE 6

[3S-[3α,6α(R*)]]-2,3,5,6,7,8-Hexahydro-6-[(2-mercapto-1-oxo-3-phenylpropyl)amino]-5-oxo-1H-azepino[3,2,1-ij]quinoline-3-carbolic acid a) 1,2,3,4-Tetrahydroquinoline-2-carboxylic acid, methyl ester, tosylate salt (S)-N-Carbobenzyloxy-1,2,3,4-tetra-hydroquinoline-2-carboxylic acid was prepared as described in U.S. Pat. No. 4,461,896. To a solution of this acid (18.743 g., 60.3 mmole) in dry dimethylformamide (70 ml.) at room temperature under argon was added powdered potassium carbonate (10.5 g., 76 mmole) and methyl iodide (5.6 ml., 12.8 g., 90.0 mmole). After stirring for 2 hours, the mixture was partitioned between ethyl acetate (200 ml.) and 5% potassium bisulfate (200 ml.). The organic phase was washed with water (twice) and brine, dried (sodium sulfate) and evaporated to dryness. The crude product was taken up in methanol (150 ml.), treated with p-toluenesulfonic acid, monohydrate (12.03 g., 63.2 mmole) and 20% palladium hydroxide on carbon (0.2 g.) and stirred-under an atmosphere of hydrogen (balloon) for 1.5 hours. The mixture was filtered through Celite and concentrated to a small volume, causing a crystalline solid to separate. This material was triturated with ethyl ether and the solid was collected to give a total of 19.965 g. of the titled product.

b) [1(S),2S]-2-Methoxycarbonyl-3,4-dihydro-γ-oxo-β-phthalimido-1(2H)-quinolinebutanoic acid, phenylmethyl ester (S)-β-Carboxy-N-phthalimidepropanoic acid, phenylmethyl ester, dicyclohexylamine salt (10.68 g., 20.0 mmole) was converted to the free acid as described in Example 1(b). This free acid was taken up in dry ethyl ether (35 ml.) and treated with phosphorus pentachloride (4.37 g., 21.0 mmole) at 0° for 30 minutes and at room temperature for 15 minutes. The resulting clear, colorless solution was evaporated, azeotroped with toluene, then taken up in toluene (40 ml.) and added dropwise to a mixture of the product from part (a) (7.986 g., 22.0 mmole) in toluene (50 ml.) and aqueous sodium bicarbonate (6.8 g. of sodium bicarbonate in 70 ml. of water.). After vigorous stirring overnight, the aqueous phase was separated and the organic phase was washed with saturated sodium bicarbonate and brine, dried (sodium sulfate), and stripped. The residue was purified by flash chromatography (LPS-1 silica gel, 160 g., 35:65-ethyl acetate:hexanes) to give 9.04 g. of the desired product as a white foam. HPLC showed a 99.4:0.6 ratio of S and R epimers of the desired product. TLC (ethyl acetate:hexanes, 40:60) $R_f$=0.36; $[\alpha]_D$=−221.4° (c=0.58, chloroform).

c) [1(S),2S]-2-Methoxycarbonyl-3,4-dihydro-γ-oxo-β-phthalimido-1(2H)-quinolinebutanoic acid A mixture of the product from part (b) (9.87 g., 18.8 mmole) and 20% palladium hydroxide on carbon (1.5 g.) in ethyl acetate (60 ml.) was hydrogenated (30 psi) in a Parr apparatus for 2 hours. The solution was filtered through Celite, washing thoroughly with acetone/methylene chloride. Removal of the solvent and crystallization of the residue from ethyl acetate/ethyl ether gave 8.152 g. of the titled product as an off-white crystalline solid; TLC (5% methanol in methylene chloride) $R_f$=0.18; $[\alpha]_D$=−247.9° (c=0.67, methanol); m.p. 188°–190°.

d) [1(S),2S]-2-Methoxycarbonyl-3,4-dihydro-γ-oxo-β-phthalimido-1(2H)-quinolinebutanethioic acid, S-ethyl ester To a suspension of the product from part (c) (7.728 g., 17.7 mmole) in methylene chloride (60 ml.) at 0° was added ethanethiol (3.4 ml., 2.85 g.,45.9 mmole), dimethylaminopyridine (440 mg., 3.6 mmole), and 1-ethyl-3-(3-dimethylaminopropyl)carbodiimide hydrochloride (3.74 g., 19.5 mmole). After stirring at 0° for one hour, additional 1-ethyl-3-(3-dimethylaminopropyl)carbodiimide hydrochloride (0.40 g.) was added and the mixture was stirred at room temperature for 2 hours. The solvent was removed in vacuo and the residue was partitioned between ethyl acetate and 5% potassium bisulfate. The ethyl acetate extract was washed successively with 5% potassium bisulfate (twice), saturated sodium bicarbonate (twice), and brine, then dried (sodium sulfate), filtered, and stripped. The residue was flash chromatographed (LPS-1 silica gel, 3:7 ethyl acetate:hexanes followed by 15:85 ethyl acetate:methylene chloride) and the pure product fractions were pooled, stripped, and crystallized from ethyl ether/hexanes to give 7.736 g. of the titled product as a white crystalline solid; TLC (methanol:methylene chloride, 1:9) $R_f$=0.88; $[\alpha]_D$=−288.4° (c=1.06, chloroform); m.p. 136°–137°.

e) [1(S),2S]-2-Methoxycarbonyl-3,4-dihydro-γ-oxo-β-phthalimido-1(2H)-quinolinebutanal To a mixture of the product from part (d) (7.605 g., 15.3 mole) and 10% palladium on carbon (1.15 g.) in dry acetonitrile (50 ml.) was added 4A molecular sieves. After stirring at room temperature for 15 minutes, triethylsilane (4.95 ml., 3.60 g., 31.0 mmole) was added dropwise over a ten minute period. After stirring for 1.5 hours, the mixture was filtered through Celite and evaporated to dryness. The residue was flash chromatographed (LPS1 silica gel, 1:9 ethyl acetate:methylene chloride) and the pure product fractions were pooled, stripped, and triturated with ethyl acetate/ethyl ether to give 4.428 g., of titled product as a white solid; TLC (ethyl acetate:hexanes, 1:1) $R_f$=0.31; $[\alpha]_D$=−239.4° (c=0.62, chloroform); m.p. 163°–164°.

f) [1S,2S]-1-(4,4-Dimethoxy-1-oxo-2 -phthalimidobutyl)-1,2,3,4-tetrahydroquinoline-2 -carboxylic acid, methyl ester To a solution of the product from part (e) (4.326 g., 10.3 mmole) in methylene chloride (20 ml.) and methanol (35 ml.) at room temperature was added trimethylorthoformate (3.5 ml.) and p-toluenesulfonic acid monohydrate (45 mg.). After stirring for 45 minutes, the reaction was quenched with saturated sodium bicarbonate (2 ml.) and evaporated to dryness. The residue was partitioned between ethyl acetate and water. The organic phase was washed with saturated sodium bicarbonate and brine, then dried (sodium sulfate), filtered, and stripped to give 4.81 g. of the titled product as a white foam; TLC (ethyl acetate:hexanes, 1:1) $R_f$=0.33; $[\alpha]_D$=−188.9° (c=0.64, chloroform).

g) (cis)-6-Phthalimido-2,3,5,6-tetrahydro-5-oxo-1H-azepino[3,2,1-ij]quinoline-3-carboxylic acid, methyl ester and (S)-6-phthlimido-2,3,5,8-tetrahydro-5-oxo-1H-azepino [3,2,1-ij]quinoline-3-carboxylic acid, methyl ester A mixture of the product from part (f) (4.627 g., 9.93 mmole) and polyphosphoric acid (46 g.) was heated at 115° (bath temperature) under argon for 2 hours. The cooled mixture was treated with ice water and the resulting tan precipitate was collected by filtration and washed with water. The solid residue was taken up in methylene chloride, washed with water, dried (sodium sulfate), and the solvent evaporated to dryness. The residue was triturated with ethyl ether to give 3.166 g. of light brown solid. In addition, 473 mg. of mother liquor was obtained. The solid was dissolved in methylene chloride (40 ml.), tetrahydrofuran (20 ml.) and methanol (5 ml.), cooled in an ice bath and treated with excess ethereal diazomethane. The mixture was then evaporated to dryness and the residue was filtered through a short column of silica gel (LPS-1) eluting with 1:9 ethyl acetate:methylene chloride. Evaporation of the solvent and trituration of the residue with ethyl ether gave 2.332 g. of nearly racemic (S)-6-phthalimido-2,3,5,8-tetrahydro-5-oxo-1H-azepino[3,2,1-ij]quinoline-3-carboxylic acid, methyl ester as a pale yellow crystalline solid; TLC (ethyl acetate:hexanes, 1:1) $R_f$=0.42; $[\alpha]_D$=−5.0° (c=0.62, chloroform); m.p. 221°–223°.

The aforementioned mother liquor was treated with ethereal diazomethane as above and the reactants were purified by flash chromatography (LPS-1 silica gel, 5:95:50 ethyl ether:methylene chloride:hexanes) to give 196 mg. of (cis)-2,3,5,6-tetrahydro-5-oxo-1H-azepino[3,2,1-ij]quinoline-3-carboxylic acid, methyl ester.

h) (cis)-2,3,5,6,7,8-Hexahydro-5-oxo-6-phthalimido-1H-azepino[3,2,1-ij]quinoline-3-carboxylic acid, methyl ester 10% Palladium on carbon (1.0 g.) was added to a suspension of (S)-6-phthalimido-2,3,5,8-tetrahydro-5-oxo-1H-azepino[3,2,1-ij]quinoline-3-carboxylic acid, methyl ester (2.084 g., 5.2 mmole) in methanol (40 ml.) and dimethylformamide (40 ml.) and the resulting mixture was hydrogenated on a Parr apparatus (50 psi, 55°) for 30 hours. The mixture was filtered through Celite® and evaporated to dryness. The crude product was purified by flash chromatography (ethyl acetate:methylene chloride:hexanes, 5:95:40 followed by ethyl acetate: methylene chloride, 5:95) to give 1.06 g. of titled product as a white solid. Recrystallization from ethyl acetate/hexanes yields an analytical sample; m.p. 128°–130°; $[\alpha]_D$=−1.1° (c=0.53, chloroform). TLC (ethyl acetate:methylene chloride, 5:95; twice developed) $R_f$=0.42.

i) (cis)-2,3,5,6,7,8-Hexahydro-5-oxo-6-amino-1H-azepino [3,2,1-ij]quinoline-3-carboxylic acid, methyl ester A solution of the product from part (h) (1.098 g., 2.7 mmole) in methanol (10 ml.) and methylene chloride (2.0 ml.) was stirred with hydrazine monohydrate (280μl, 289 mg., 5.8 mmole) at room temperature for 48 hours. The mixture was diluted with ethyl acetate, filtered, and stripped. The residue was flash chromatographed (LPS-1 silica gel, methanol:methylene chloride, 5:95) and the pooled product fractions were stripped and crystallized from ethyl acetate/hexane to give 574 mg. of titled product as a highly crystalline solid; m.p. 101°–102°. TLC (methanol:methylene chloride, 5:95) $R_f$=0.29.

j) [3S-[3α,6α(R*)]]-2,3,5,6,7,8-Hexahydro-6-[[2-(acetylthio)-1-oxo-3-phenylpropyl]amino]-5-oxo-1H-azepino[3,2,1-ij]quinoline-3-carboxylic acid, methyl ester and its [3S-[3α,6α(S*)]]diastereomer (S)-2-(Acetylthio)benzenepropanoic acid, dicyclohexylamine salt (745 mg., 1,84 mmole) was partitioned between ethyl acetate (25 ml.) and 5% potassium bisulfate (215 ml.). The ethyl acetate extract was washed with additional 5% potassium bisulfate and brine, dried (sodium sulfate), filtered and stripped to afford the free acid as an oil. This acid was dissolved in dry methylene chloride (10 ml.), cooled to 0°, and treated successively with the product from part (i) (480 mg., 1.75 mmole), triethylamine (255 µl., 186 mg., 1.84 mmole), and benzotriazol-1-yloxy-tris(dimethylamino)phosphonium hexafluorophosphate (830 mg., 1.88 mmole). After stirring at 0° for 3 hours, the solvent was removed by rotary evaporation and the residue was partitioned between ethyl acetate and 5% potassium bisulfate. The ethyl acetate extract was washed with saturated sodium bicarbonate and brine, then dried (sodium sulfate), filtered and stripped. The residue was purified by flash chromatography (LPS-1 silica gel, ethyl acetate:hexanes, 35:65) to give 340 mg. of [3S-[3α,6α(R*)]]-2,3,5,6,7,8-hexahydro-6-[[2 -acetylthio)-1-oxo-3-phenylpropyl]amino]-5-oxo-1H-azepino[3,2,1-ij] quinoline-3-carboxylic acid, methyl ester; $[\alpha]_D = -247.6°$ (c=0.55, chloroform); TLC (ethyl acetate:hexanes, 4:6) $R_f = 0.26$ and 342 mg. of [3S-[3α,6α(S*)]]-2,3,5,6,7,8-hexahydro-6-[[2 -(acetylthio)-1-oxo-3-phenylpropyl] amino]-5-oxo-1H-azepino[3,2,1-ij]quinoline-3-carboxylic acid, methyl ester; $[\alpha]_D = +162.0°$ (c=0.54, chloroform); TLC (ethyl acetate:hexanes, 4:6) $R_f = 0.20$.

k) [3S-[3α,6α(R*)]]-2,3,5,6,7,8-Hexahydro-6-[2 -mercapto-1-oxo-3-phenylpropyl)amino]-5-oxo-1H-azepino[3,2,2-ij]quinoline-3-carboxylic acid To a de-oxygenated (argon purged) solution of the [3S-[3α,6α(R*)]]product from part (j) (312 mg., 0.65 mmole) in methanol (5 ml.) at 0° was added deoxygenated 1N sodium hydroxide (5 ml.). Argon was passed through the mixture during the course of the reaction. After 2.5 hours at 0°, the solution was acidified with concentrated hydrochloric acid (0.7 ml.) and extracted with ethyl acetate. The ethyl acetate extract was washed with brine, dried (sodium sulfate), filtered, and stripped. The residue was triturated with ethyl ether/hexanes to give 272 mg. of titled product as a white solid; $[\alpha]_D = -247.1°$ (c=0.51, methanol); TLC (acetic acid:methanol:methylene chloride, 1:1:40) $R_f = 0.29$.

Anal. calc.d. for $C_{23}H_{24}N_2O_4S \cdot 0.47$ $H_2O$: 0.14 $C_4H_{10}O \cdot 0.09$ $C_6H_{14}$: C, 64.17; H, 6.17; N, 6.21; S, 7.11 Found: C, 64.17; H, 5.98; N, 6.20; S, 6.97.

EXAMPLE 7

1000 tablets each containing the following ingredients:

| | |
|---|---|
| [3S-[3α,6α(R*)]]-2,3,5,6,7,8-Hexahydro-6-[(2-mercapto-1-oxo-3-phenylpropyl)amino]-5-oxo-1H-azepino]3,2,1-ij]quinoline-3-carboxylic acid | 200 mg. |
| Cornstarch | 100 mg. |
| Gelatin | 20 mg. |
| Avicel(microcrystalline cellulose) | 50 mg. |
| Magnesium stearate | 5 mg. |
| | 375 mg. | are prepared from sufficient bulk quantities by mixing the product of Example 6 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 200 mg. of active ingredient.

In a similar manner, tablets containing 200 mg. of the product of any of Examples 1 to 5 can be prepared.

Similar procedures can be employed to form tablets of capsules containing from 50 mg. to 500 mg. of active ingredient.

What is claimed is:

1. A compound of the formula

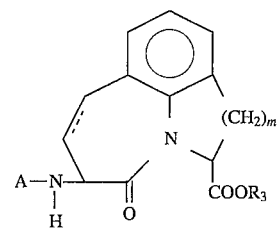

including a pharmaceutically acceptable salt thereof wherein:

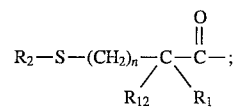

$R_1$ and $R_{12}$ are independently selected from the group consisting of hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen,

or $R_{11}$—S—;

$R_3$ is selected from the group consisting of hydrogen, alkyl, substituted alkyl, aryl-$(CH_2)_p$—, substituted aryl-$(CH_2)_p$—, heteroaryl-$(CH_2)_p$—

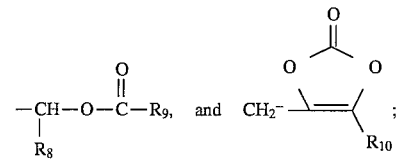

$R_6$ is alkyl, substituted alkyl, cycloalkyl-$(CH_2)_p$—, aryl-$(CH_2)_p$—, substituted aryl-$(CH_2)_p$—, or heteroaryl-$(CH_2)_p$—;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl-$(CH_2)_p$—;

$R_{11}$ is alkyl, substituted alkyl, cycloalkyl-$(CH_2)_p$—, aryl-$(CH_2)_p$—, substituted aryl-$(CH_2)_p$—, heteroaryl-$(CH_2)_p$—, or —S—$R_{11}$ completes a symmetrical disulfide wherein $R_{11}$ is

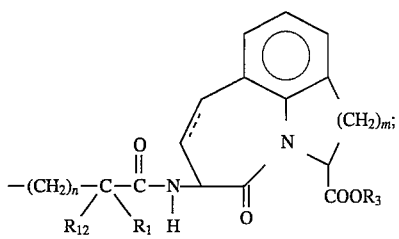

m is one or two;
n is zero or one;
p is zero or an integer from 1 to 6; and
the dashed line - - - represents an optional double bond between the two carbons.

2. A compound of claim 1 of the formula

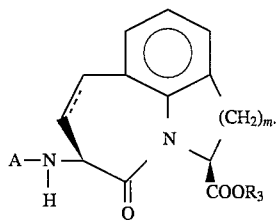

3. A compound of claim 2 of the formula

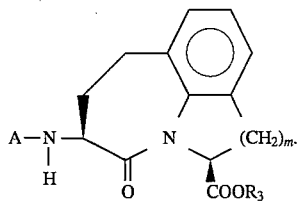

4. A compound of claim 2 wherein:
$R_2$ is hydrogen

or $R_{11}$—S—;
$R_3$ is hydrogen or lower alkyl of 1 to 4 carbons;
n is zero or one;
$R_{12}$ is hydrogen;
$R_{11}$ is lower alkyl or 1 to 4 carbons;
$R_1$ is aryl-$CH_2$—, substituted aryl-$CH_2$—, heteroaryl-$CH_2$—, cycloalkyl-$CH_2$— wherein cycloalkyl is of 5 to 7 carbons, or straight or branched chain alkyl of 1 to 7 carbons;
$R_6$ is lower alkyl of 1 to 4 carbons or phenyl; and
m is one or two.

5. A compound of claim 4 wherein:
$R_2$ is hydrogen; and
$R_1$ is benzyl.

6. The compound of claim 5 wherein:
n is zero; and
m is one.

7. The compound of claim 6, [2S-[2α,5α(R*)]]-1,2,4,5,6,7-hexahydro-5-[(2-mercapto-1-oxo-3-phenylpropyl)amino]-4-oxoazepino[3,2,1-hi]indole-2-carboxylic acid.

8. The compound of claim 5 wherein:
n is one; and m is one.

9. The compound of claim 8, [2S-[2α,5α(R*)]]-1,2,4,5,6,7-hexahydro-5-[[2-(mercaptomethyl)-1-oxo-3-phenylpropyl]amino]-4-oxoazepino[3,2,1-hi]indole-2-carboxylic acid.

10. The compound of claim 5 wherein:
n is zero; and
m is two.

11. The compound of claim 10, [3S-[3α,6α(R*)]]-2,3,5,6,7,8-hexahydro-6-[(2-mercapto-1-oxo-3-phenylpropyl)amino]-5-oxo-1H-azepino[3,2,1-ij]quinoline-3-carboxylic acid.

12. A compound of claim 4 wherein:
$R_2$ is hydrogen; and
$R_1$ is 1-naphthyl.

13. The compound of claim 12 wherein:
n is zero; and
m is one.

14. The compound of claim 13, [2S-(2α,5α)]]-1,2,4,5,6,7-hexahydro-5-[[2-mercapto-1-oxo-3-(1-naphthalenyl)propyl]amino]-4-oxoazepino[3,2,1-hi]indole-2-carboxylic acid.

15. A compound of claim 2 of the formula

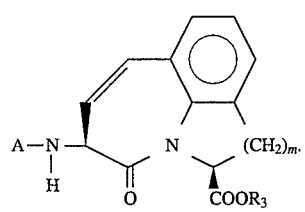

16. A compound of claim 15 wherein:
$R_2$ is hydrogen,

or $R_{11}$—S—;
$R_3$ is hydrogen or lower alkyl of 1 to 4 carbons;
n is zero or one;
$R_{12}$ is hydrogen;
$R_{11}$ is lower alkyl or 1 to 4 carbons;
$R_1$ is aryl-$CH_2$—, substituted aryl-$CH_2$—, heteroaryl-$CH_2$—, cycloalkyl-$CH_2$— wherein cycloalkyl is of 5 to 7 carbons, or straight or branched chain alkyl of 1 to 7 carbons;
$R_6$ is lower alkyl of 1 to 4 carbons or phenyl; and
m is one or two.

17. A compound of claim 16 wherein:
$R_2$ is hydrogen; and
$R_1$ is benzyl.

18. The compound of claim 17 wherein:
n is zero; and
m is one.

19. The compound of claim 18, [2S-[2α,5α(R*)-1,2,4,5-tetrahydro-5-[(2-mercapto-1-oxo-3-phenylpropyl)amino]-4-oxoazepino[3,2,1-hi]indole-2-carboxylic acid.

20. The compound of claim 17 wherein:
n is one; and
m is one.

21. The compound of claim 20, [2S-[2α,5α(R*)]]-1,2,4,5-tetrahydro-5-[[2-(mercaptomethyl)-1-oxo-3-phenylpropyl]amino]-4-oxoazepino[3,2,1-hi]indole-2-carboxylic acid.

22. A pharmaceutical composition useful in the treatment of cardiovascular disease such as hypertension and congestive heart failure comprising a pharmaceutically acceptable carrier and one or more compounds of the formula

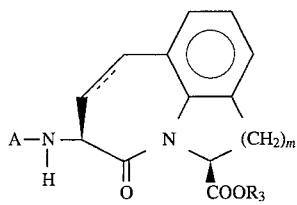

including a pharmaceutically acceptable salt thereof wherein m, A, $R_3$, and the dashed line are as defined in claim 1.

23. A method of treating cardiovascular diseases such as hypertension and congestive heart failure in a mammalian species which comprises administering an effective amount of the composition of claim 22.

24. A compound of the formula

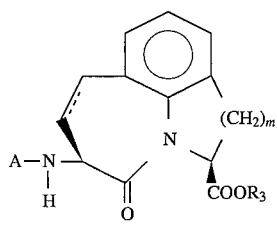

including a pharmaceutically acceptable salt thereof wherein:

A is

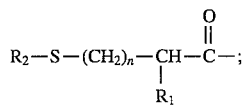

$R_1$ is hydrogen, alkyl, cycloalkyl-$(CH_2)_p$—, substituted alkyl, aryl-$(CH_2)_p$—, substituted aryl-$(CH_2)_p$—, or heteroaryl-$(CH_2)_r$—;

$R_2$ is hydrogen or

$R_3$ is hydrogen, lower alkyl, aryl-$(CH_2)_r$—,

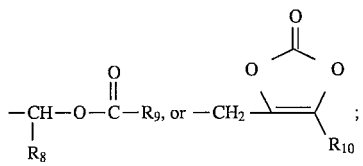

$R_6$ is alkyl, substituted alkyl, cycloalkyl-$(CH_2)_p$—, aryl-$(CH_2)_p$—, substituted aryl-$(CH_2)_p$—, or heteroaryl-$(CH_2)_p$—;

$R_8$ is hydrogen, lower alkyl, cycloalkyl, or phenyl;
$R_9$ is hydrogen, lower alkyl, lower alkoxy, or phenyl;
$R_{10}$ is lower alkyl or aryl-$(CH_2)_r$—;
m is one or two;
n is zero or one,
p is zero or an integer from 1 to 6;
r is an integer from 1 to 6; and
the dashed line - - - represents an optional double bond between the two carbons.

25. A compound of the formula

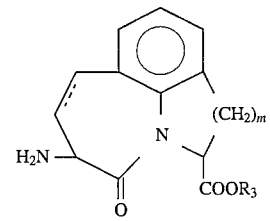

including a salt thereof wherein:

$R_3$ is hydrogen, lower alkyl, or aryl-$(CH_2)_p$—;
p is zero or an integer from 1 to 6;
m is one or two; and the dashed line - - - represents an optional double bond between the two carbons.

26. A compound of claim 25 of the formula

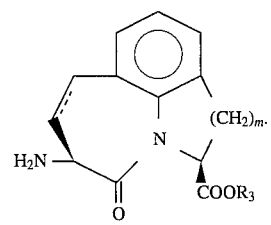

27. The compound of claim 26

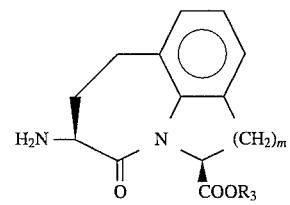

wherein:
$R_3$ is lower alkyl; and
m is one or two.

28. The compound of claim 27 wherein
$R_3$ is ethyl; and
m is one.

29. The compound of claim 27 wherein
$R_3$ is methyl; and
m is two.

30. The compound of claim 26

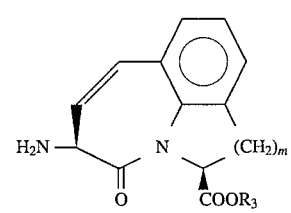

wherein:
$R_3$ is lower alkyl; and
m is one or two.

31. The compound of claim 30 wherein:
$R_3$ is ethyl; and
m is one.

* * * * *